(12) United States Patent
Uk

(10) Patent No.: US 6,723,128 B2
(45) Date of Patent: Apr. 20, 2004

(54) PROSTHETIC DEVICE FOR CORRECTING DEFORMITY OF SPINE

(76) Inventor: Chang Jong Uk, 908 dong A-APT Chun-Ho 3-Dong Kang Dong-Ku, Seoul (KR)

( * ) Notice: Subject to any disclaimer, the term of this patent is extended or adjusted under 35 U.S.C. 154(b) by 0 days.

(21) Appl. No.: 09/932,799

(22) Filed: Aug. 20, 2001

(65) Prior Publication Data
US 2002/0045943 A1 Apr. 18, 2002

(51) Int. Cl.$^7$ .................................................. A61F 2/44
(52) U.S. Cl. .................................................. 623/17.15
(58) Field of Search .................. 623/17.15, 17.11, 623/16.11, 11.11

(56) References Cited

U.S. PATENT DOCUMENTS

| | | | | |
|---|---|---|---|---|
| 4,863,476 | A | * | 9/1989 | Shepperd |
| 5,360,450 | A | * | 11/1994 | Giannini |
| 5,554,191 | A | * | 9/1996 | Lahille et al. ............ 623/17.11 |
| 5,653,763 | A | * | 8/1997 | Errico et al. ............. 623/17.11 |
| 5,782,919 | A | | 7/1998 | Zdeblick et al. |
| 6,129,763 | A | * | 10/2000 | Chauvin et al. .......... 623/17.11 |
| 6,190,414 | B1 | * | 2/2001 | Young et al. ............. 623/17.15 |
| 6,436,140 | B1 | * | 8/2002 | Liu et al. ................. 623/17.11 |
| 2002/0068977 | A1 | * | 6/2002 | Jackson .................... 623/17.15 |

* cited by examiner

Primary Examiner—Jeffrey A. Smith
(74) Attorney, Agent, or Firm—Leighton K. Chong; Ostrager Chong & Flaherty

(57) ABSTRACT

The present invention discloses a prosthetic device for correcting deformity of the spine including a prosthetic device main body being inserted into an intervertebral disk, and having a variable height to correct deformity of the spine, and a control strip inserted into the prosthetic device main body, for controlling a height of the prosthetic device main body. A control strip insertion hole where the control strip is inserted and fixed is formed at the center portion of a height variable surface of the prosthetic device main body, an insertion hole is formed at the rear side portion of the prosthetic device main body which faces the variable surface, and an elastic cutting groove having a variable width is extended in a lateral direction from the control strip insertion hole to the rear surface, for dividing the variable surface into the upper and lower portions. The control strip is rotatably aligned in the control strip insertion hole of the prosthetic device main body, for enabling the variable surface to have an initial insertion position and a maximum height position by the rotation. Two prosthetic devices are inserted into the intervertebral disk of the spine, and fixed at a predetermined angle. As a result, the prosthetic device is easily safely inserted and fixed into a suitable position in a spine operation.

1 Claim, 4 Drawing Sheets

PROSTHETIC DEVICE FOR CORRECTING DEFORMITY OF SPINE

BACKGROUND OF THE INVENTION

1. Field of the Invention

The present invention relates to a prosthetic device for correcting deformity of the spine. In particular, the present invention relates to an improved prosthetic device for correcting deformity of the spine which includes a prosthetic device main body having a height variable surface at its one side to easily insert and fix the prosthetic device into a suitable position of the spine in a spine operation, by inserting the prosthetic device into an intervertebral disk of the spine and fixing it at an appropriate angle, and a control strip rotatably aligned in a control strip insertion hole of the prosthetic device main body, for enabling the variable surface to have an initial insertion position and a maximum height position by one rotation.

2. Description of the Related Art

In a conventional prosthetic device for correcting deformity of the spine, a prosthetic device main body has a protrusion which does not vary a height, and an operation hammer is used for a spine operation. It is thus difficult to insert and fix the prosthetic device into a presumed position of an intervertebral disk of the spine. Accordingly, the prosthetic device is inserted into an adjacent position to the presumed position of the spine. In addition, a normal bone may be cut due to an inappropriate angle of the spine inserted. In order to overcome the foregoing problems, there has been suggested a prosthetic device variably extending its front head portion inserted into an intervertebral disk of the spine. In the prosthetic device, a through hole having a helix is formed at the center portion of a prosthetic device main body, and a disc-shaped rotating body serving as a bolt is rotated along the helix of the through hole a few tens times, so that the front head portion of the prosthetic device can be variably extended to correct deformity of the spine. Nevertheless, the foregoing problems are not fully overcome. That is, the prosthetic device is inserted and fixed into the intervertebral disk, but the prosthetic device is hard to move at the time of changing an operation position. In addition, the through hole having the helix is formed at the center portion of the prosthetic device main body, and thus the prosthetic device is fixed to or removed from the spine merely through the rotation. Accordingly, it is difficult to remove the fixed prosthetic device in the re-operation of the spine.

SUMMARY OF THE INVENTION

Accordingly, it is an object of the present invention to provide a prosthetic device for correcting deformity of the spine which can control a height of a variable surface of a prosthetic device main body to fix the prosthetic device at a maximum height by a single rotation, by inserting and fixing a control strip for controlling the height of the variable surface into a control strip insertion hole of the prosthetic device main body.

In order to achieve the above-described object of the invention, there is provided a prosthetic device for correcting deformity of the spine which can be fixed to and removed from the spine by a single rotation, so that an operation for fixing the spine by inserting and extending the prosthetic device can be safely rapidly performed.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENT

Figure 1:
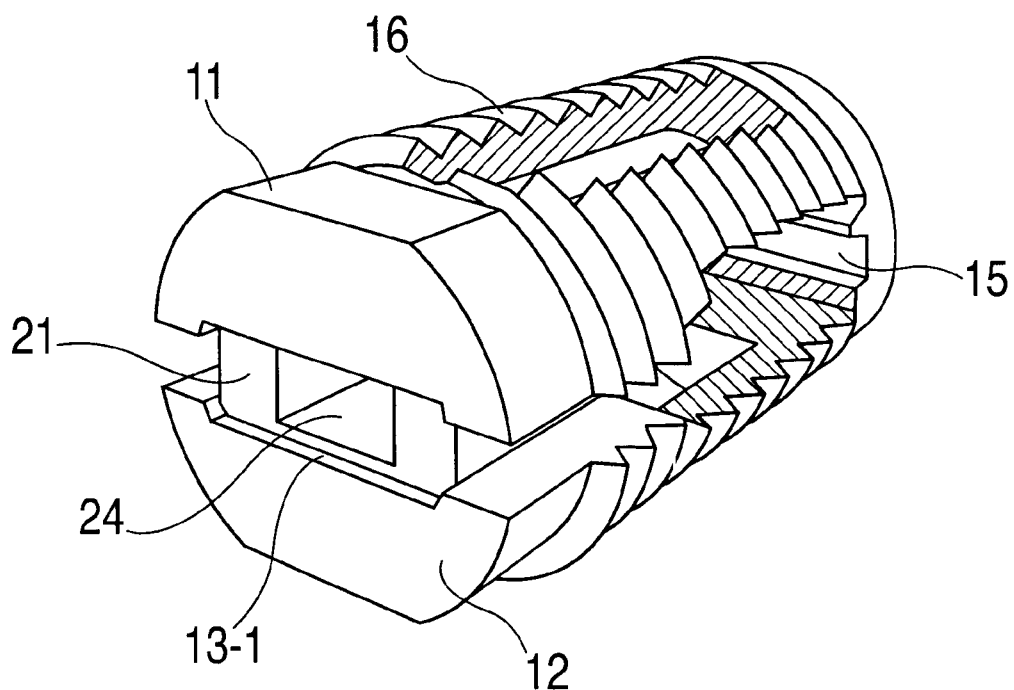
FIG. 1 is a perspective view illustrating a prosthetic device for correcting deformity of the spine in accordance with the present invention.
Figure 2:
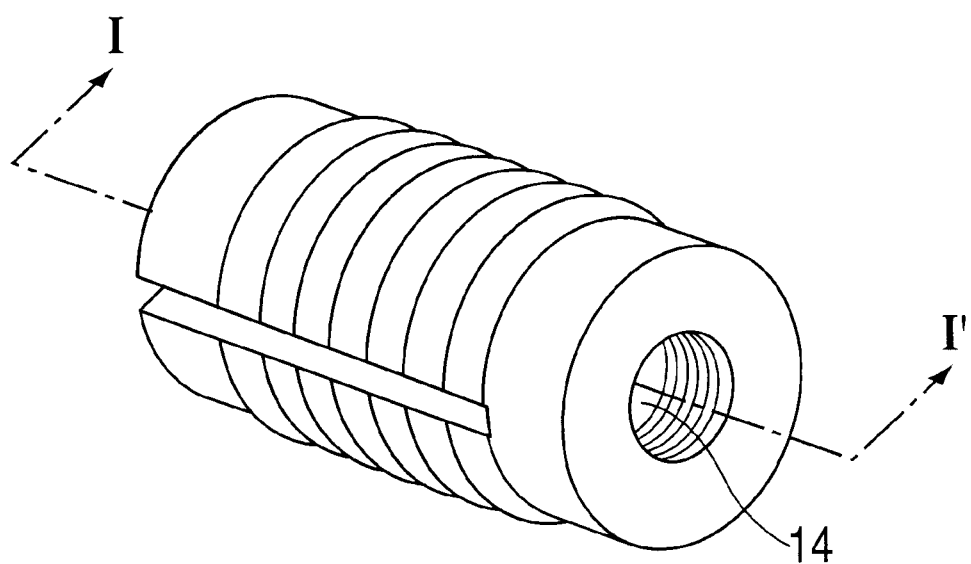
FIG. 2 is a perspective view illustrating the rear portion of the prosthetic device of FIG. 1.
Figure 3:
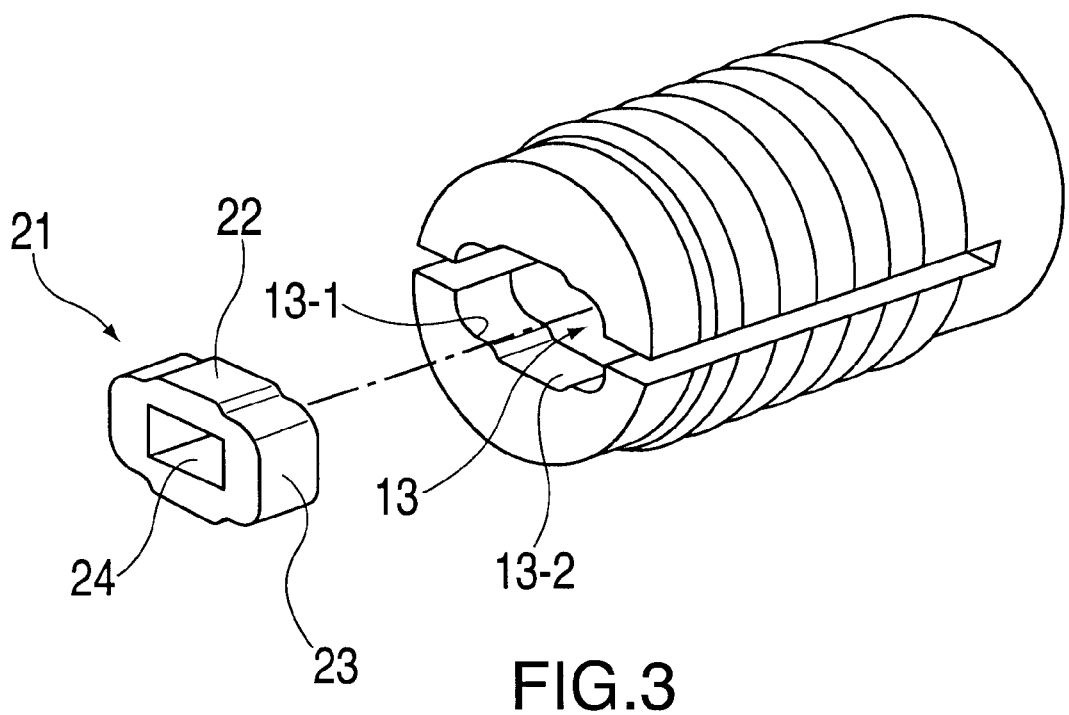
FIG. 3 is a perspective view illustrating a disassembling state of the prosthetic device of FIG. 1.
Figure 4:
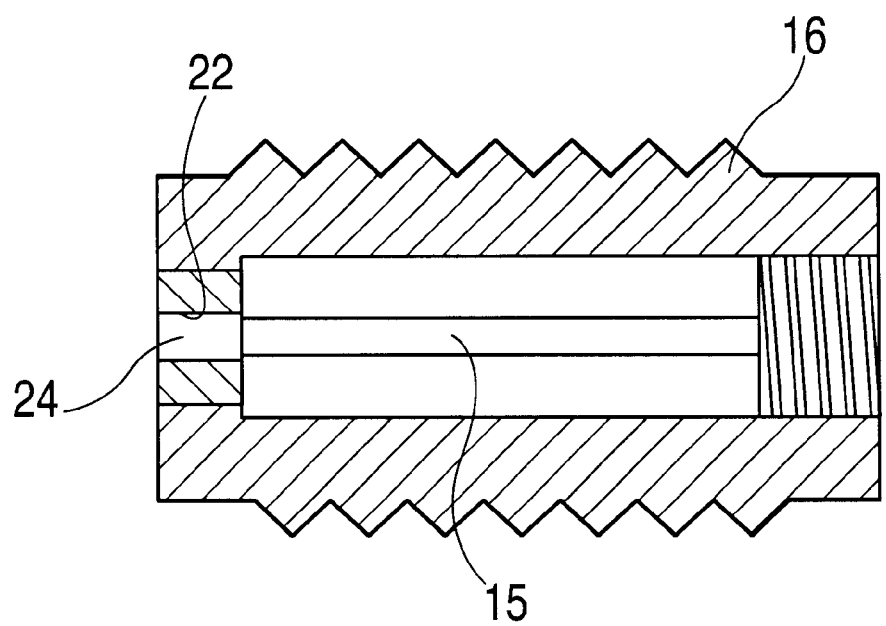
FIG. 4 is a cross-sectional view illustrating the prosthetic device, taken along line I—I' of FIG. 2.

A prosthetic device for correcting deformity of the spine in accordance with preferred embodiments of the present invention will now be described with reference to the accompanying drawings.

As illustrated in FIGS. 1 through 8, the prosthetic device A includes a prosthetic device main body 11 being inserted into an intervertebral disk, and having a variable height to correct deformity of the spine, and a control strip 21 inserted into the prosthetic device main body 11, for controlling a height of the prosthetic device main body 11. A control strip insertion hole 13 where the control strip 21 is inserted and fixed is formed at the center portion of a height variable surface 12 of the prosthetic device main body 11. An insertion hole 14 is formed at the rear side portion of the prosthetic device main body 11 which faces the variable surface 12. An elastic cutting groove 15 having a variable width is extended in a lateral direction from the control strip insertion hole 13 to the rear surface, for dividing the variable surface 12 into the upper and lower portions. The control strip 21 is rotatably aligned in the control strip insertion hole 13 of the prosthetic device main body 11. Here, an initial insertion position fixing surface 22 for controlling a height of the variable surface 12 of the prosthetic device main body 11, a maximum height fixing surface 23 and a control groove 24 are incorporated and fixed to the control strip insertion hole 13 of the prosthetic device main body 11 at a maximum height by a single rotation, for controlling a height of the variable surface of the prosthetic device main body 11.

The prosthetic device main body 11 is formed in a circular cylinder shape having a plurality of hook protrusions 16 advanced in a forward direction in rotation, or in a polyprism shape having a plurality of hook protrusions 16' at the right and left side portions of the upper and lower ends.

A fixing jaw 13-1 is protruded along the curved line of the cutting surface of the control strip insertion hole 13 of the prosthetic device main body 11, for supporting the inserted control strip 21. A cutting groove 13-2 is formed at a maximum height fixing position of the control unit of the control strip 21, for firmly fixing the control strip 21.

In addition, an indication rod (not shown) having a male screw to insert the prosthetic device into the intervertebral disk of the spine is fixed to a female screw 14-1 of an insertion hole 14 of the rear side portion of the prosthetic device main body 11, and a driver (not shown) is inserted into a control groove formed at the center portion of one side of the control strip 21 in order to control the height of the variable surface of the prosthetic device main body 11 by rotating the control strip 21.

The prosthetic device for correcting deformity of the spine in accordance with one preferred embodiment of the present invention will now be explained.

Figure 5:
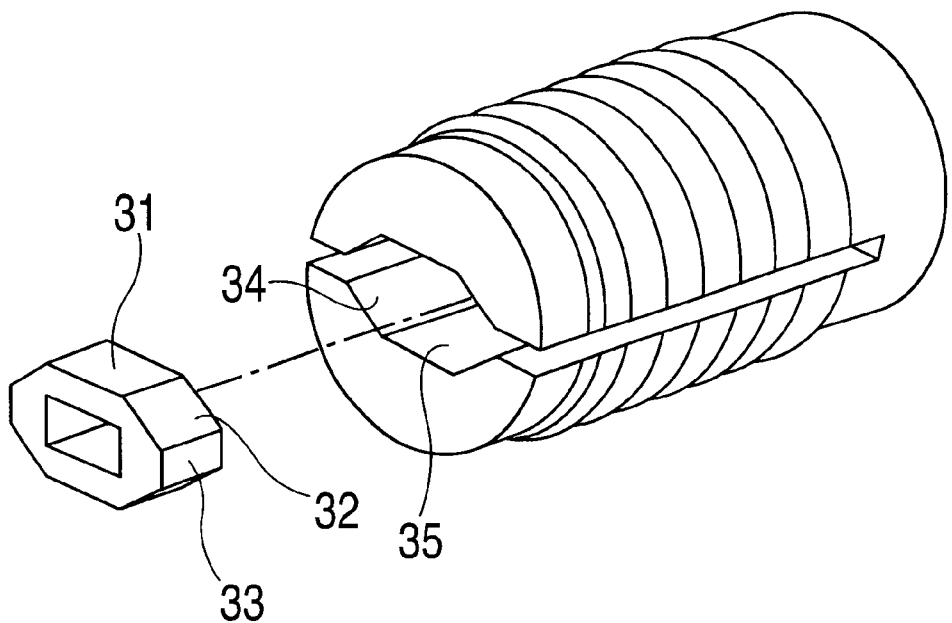
FIG. 5 is a perspective view illustrating a prosthetic device for correcting deformity of the spine in accordance with one preferred embodiment of the present invention.
Figure 6:
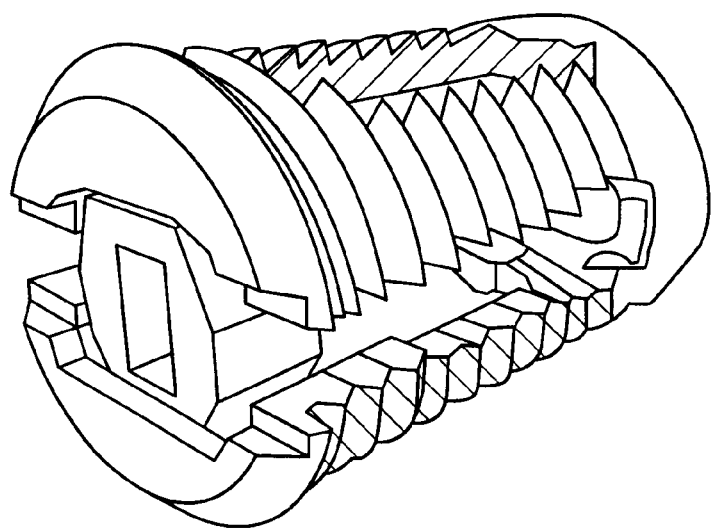
FIG. 6 is a perspective view showing a state where the prosthetic device of FIG. 5 is operated at a maximum height.
Figure 7:
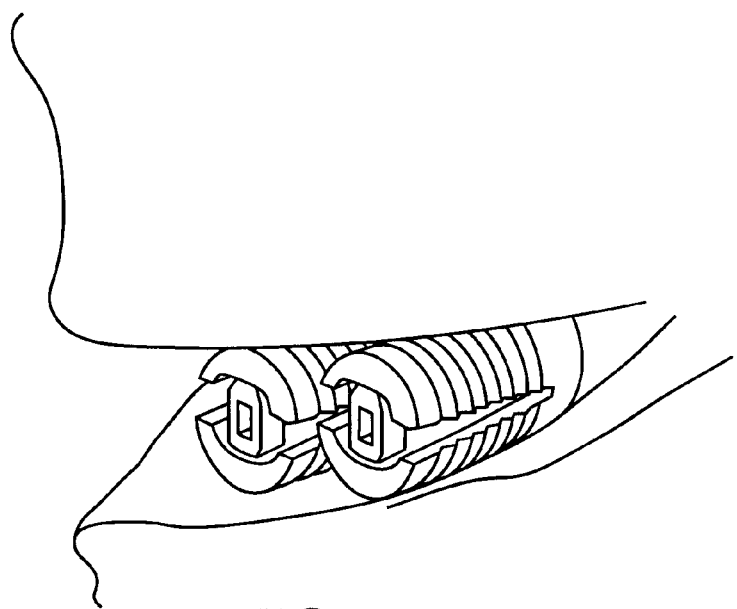
FIG. 7 is a perspective view illustrating an operation state of the prosthetic device in accordance with the present invention.
Figure 8:
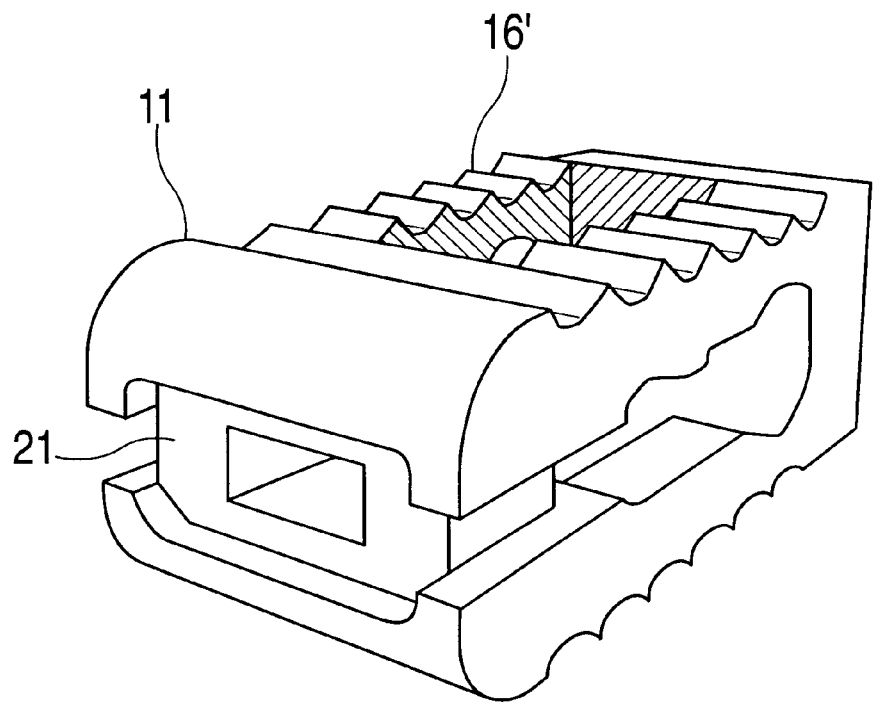
FIG. 8 is a perspective view showing a state where a polyprism-shaped prosthetic device is operated at a maximum height.

Referring to FIG. 5, the control strip is formed in various shapes such as a polygon. The control strip is rotated at a predetermined angle to be fixed into the control strip insertion hole of the prosthetic device main body, so that the height of the variable surface of the prosthetic device main body 11 can be variably controlled according to a length of the control strip. As compared with the conventional control strip fixed to the control strip insertion hole of the prosthetic device main body at a maximum height by a single rotation, the control strip of the present invention has a variable height by two or three rotations. That is, the initial position fixing surface 31 of the control strip is fixed to an initial position, the middle height position fixing surface 32 is fixed to the cutting groove 34 of the control strip insertion hole, and the maximum height position fixing surface 33 is fixed to the inside cutting groove 35 of the cutting groove of the control strip insertion hole.

The operation of the prosthetic device for correcting deformity of the spine in accordance with one preferred embodiment of the present invention will now be explained. The prosthetic device includes the prosthetic device main body having a variable height to insert the prosthetic device into the intervertebral disk for correcting deformity of the spine, and the control strip inserted into the prosthetic device main body, for controlling the height of the prosthetic device main body. The circular cylinder-shaped indication rod (not shown) having the male screw at its circumferential portion and the through hole at its center portion is fixed to the female screw of the insertion hole of the rear side portion of the prosthetic device main body, thereby pushing the circular cylinder-shaped or polyprism-shaped prosthetic device into the intervertebral disk by rotation or in a straight line. The driver (not shown) is inserted into the control groove of the control strip through the through hole of the center portion of one side of the indication rod, thereby adjusting the control strip at a maximum length by a single rotation. Accordingly, the maximum height position fixing surface of the control strip is fixed to the cutting groove of the control strip insertion hole, the elastic cutting groove having a variable width is widened, and the variable unit of the prosthetic device main body inserted into and supported by the intervertebral disk is adjusted at a maximum height. Thereafter, the plurality of forwardly-protruded hook protrusions 16 or the plurality of hook protrusions 16' formed at the right and left side portions of the upper and lower ends of the polyprism-shaped prosthetic device main body are firmly fixed to the intervertebral disk of the spine, thereby correcting deformity of the spine. Then, the indication rod is removed, to easily firmly fix the prosthetic device in the spine operation.

Although the preferred embodiment of the present invention has been described, it is understood that the present invention should not be limited to these preferred embodiments but various changes and modifications can be made by one skilled in the art within the spirit and scope of the present invention as hereinafter claimed.

As discussed earlier, in accordance with the present invention, the control strip is rotatably aligned in the control strip insertion hole of the prosthetic device main body, the prosthetic device main body includes the variable unit having a variable height to insert the prosthetic device into the intervertebral disk for correcting deformity of the spine, and the control groove, the initial insertion position fixing surface for controlling the height of the variable surface of the prosthetic device main body, and the maximum height position fixing surface are incorporated in the control strip, thereby adjusting the variable unit of the prosthetic device main body at a maximum height by a single rotation. That is, the height of the variable surface of the prosthetic device to be inserted into the intervertebral disk of the spine is measured according to the growth of a patient, and thus the control strip having a suitable length is inserted into the control strip insertion hole of the variable surface of the prosthetic device main body. As a result, the operation can be precisely rapidly performed on the spine by one rotation on the basis of the previously-measured height of the variable surface. Moreover, the prosthetic device is fixed to the intervertebral disk by a simple operation, which results in a simplified structure. It is also economically advantageous merely by varying a shape of the control strip.

What is claimed is:

1. A prosthetic device for correcting deformity of the spine comprising:

a prosthetic device main body for being inserted into an intervertebral disk, and having a variable height to correct deformity of the spine; and a control strip inserted into the prosthetic device main body, for controlling a height of the prosthetic device main body;

a control strip insertion hole formed at a front side of the prosthetic device main body where the control strip is inserted having upper and lower surfaces which are movable apart for varying the height of the prosthetic device main body;

an insertion hole formed at a rear side of the prosthetic device main body which faces opposite the control strip insertion hole surface;

an elastic groove cut into lateral sides of the prosthetic device main body having a variable width along a longitudinal direction from the front side to the rear side of the prosthetic device main body and dividing the upper and lower surfaces of the control strip insertion hole; and the control strip being rotatable to different alignment positions in the control strip insertion hole of the prosthetic device main body for varying the height of the prosthetic device main body by rotation thereof, wherein the control strip is rotatable from an initial insertion position in the control strip insertion hole to a maximum height position spreading the groove to a maximum width to vary the height of the prosthetic device main body to a maximum height by a single rotation, and wherein the control strip is formed in a polyprism shape having a given length and is rotatable to a predetermined angle so that the height of the prosthetic device main body can be controlled according to the length of the control strip.

* * * * *